United States Patent
Haga et al.

(10) Patent No.: US 7,465,827 B2
(45) Date of Patent: Dec. 16, 2008

(54) PROCESS FOR PRODUCING 2-HYDROXY-4-METHYLTHIOBUTYRIC ACID

(75) Inventors: Toru Haga, Ehime (JP); Tetsuya Shiozaki, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/573,728

(22) PCT Filed: Aug. 12, 2005

(86) PCT No.: PCT/JP2005/015113

§ 371 (c)(1),
(2), (4) Date: Feb. 15, 2007

(87) PCT Pub. No.: WO2006/019149

PCT Pub. Date: Feb. 23, 2006

(65) Prior Publication Data

US 2007/0213560 A1    Sep. 13, 2007

(30) Foreign Application Priority Data

Aug. 18, 2004  (JP) ............................. 2004-238002

(51) Int. Cl.
*C07C 323/00* (2006.01)
(52) U.S. Cl. ..................................... 562/581
(58) Field of Classification Search ............. None
See application file for complete search history.

(56) References Cited

U.S. PATENT DOCUMENTS

| 4,912,257 | A |   | 3/1990  | Hernandez et al. |
| 5,976,609 | A |   | 11/1999 | Hasseberg et al. |
| 6,008,409 | A | * | 12/1999 | Hasseberg et al. .......... 562/581 |
| 6,743,946 | B1|   | 6/2004  | Carencotte et al. |
| 6,815,560 | B1|   | 11/2004 | Garrait et al. |

FOREIGN PATENT DOCUMENTS

| EP | 0 142 488 A2 | 5/1985 |
| EP | 0 143 100 A2 | 5/1985 |
| EP | 0 863 135 A2 | 9/1998 |
| EP | 1 266 885 A1 | 12/2002 |
| JP | 60-166661 A | 8/1985 |
| JP | 2001-226344 A | 8/2001 |
| JP | 2002-255927 A | 9/2002 |
| JP | 2002-293770 A | 10/2002 |
| WO | WO 96/40630 A1 | 12/1996 |
| WO | WO 00/46190 A1 | 8/2000 |
| WO | WO 02/08181 A1 | 1/2002 |

\* cited by examiner

*Primary Examiner*—Paul A Zucker
(74) *Attorney, Agent, or Firm*—Sughrue Mion, PLLC

(57) ABSTRACT

The present invention provides a process for producing 2-hydroxy-4-methylthiobutyric acid comprising the following steps (1) to (4):

(1): hydrolyzing 2-hydroxy-4-methylthiobutyronitrile in the presence of sulfuric acid,
(2): separating the reaction mixture obtained in the step (1) into an oil layer containing 2-hydroxy-4-methylthiobutyric acid and a water layer,
(3): concentrating the oil layer obtained in the step (2), and
(4) heating the concentrated product obtained in the step (3).

3 Claims, No Drawings

PROCESS FOR PRODUCING 2-HYDROXY-4-METHYLTHIOBUTYRIC ACID

BACKGROUND OF THE INVENTION

1. Technical Field

The present invention relates to a process for producing 2-hydroxy-4-methylthiobutyric acid usable for a feed additive for animals.

2. Description of the Related Art

Conventionally, as a process for producing 2-hydroxy-4-methylthiobutyric acid have been known processes of hydration and hydrolysis reaction of 2-hydroxy-4-methylthiobutyronitrile in the presence of sulfuric acid (e.g., reference to EP-A-0142488, EP-A-0143100, U.S. Pat. No. 4,912,257, U.S. Pat. No. 5,976,609, WO 96/40630, U.S. Pat. No. 6,815,560, U.S. Pat. No. 6,743,946, WO 00/46190, WO 02/08181, EP-A-0863135, EP-A-1266885, JP-A-2002-255927, and JP-A-2002-293770). In these processes, generally after oil-water separation of hydration and hydrolysis reaction mixtures is carried out, the oil layer is concentrated to obtain 2-hydroxy-4-methylthiobutyric acid as a product.

SUMMARY OF THE INVENTION

However, in the above-mentioned conventional processes, when the oil layer is concentrated.

2-hydroxy-4-methylthiobutyric acid is subjected to dehydration-condensation with sulfate contained in a slight amount in the oil layer to form a sulfate ester (1-carboxy-3-methylthiopropyl sulfate) aside and it sometimes becomes a problem in terms of the product.

The present invention aims to provide a process for producing 2-hydroxy-4-methylthiobutyric acid having high quality with a suppressed amount of the sulfate ester produced aside.

That is, the present invention provides a process for producing 2-hydroxy-4-methylthiobutyric acid comprising the following steps (1) to (4);

(1): hydrolyzing 2-hydroxy-4-methylthiobutyronitrile in the presence of sulfuric acid,
(2): separating the reaction mixture obtained in the step (1) into an oil layer containing 2-hydroxy-4-methylthiobutyric acid and a water layer,
(3): concentrating the oil layer obtained in the step (2), and
(4): heating the concentrated product obtained in the step (3).

According to the present invention, it is made possible to produce high quality 2-hydroxy-4-methylthiobutyric acid with a suppressed amount of sulfuric acid ester produced aside.

DETAILED DESCRIPTION OF THE PREFERRED EMBODIMENTS

Hereinafter, the present invention will be described in detail. In the present invention, a reaction mixture containing 2-hydroxy-4-methylthiobutyric acid is obtained by hydrolyzing 2-hydroxy-4-methylthiobutyronitrile used as a raw material in the presence of sulfuric acid [step (1)]. In this reaction, since ammonium sulfate and ammonium bisulfate are produced, these ammonium salts of sulfuric acid are also contained in the reaction mixture. The production ratio of ammonium sulfate and ammonium bisulfate differs in accordance with the use amount of sulfuric acid and reaction rate.

The raw material, 2-hydroxy-4-methylthiobutyronitrile, can be prepared, for example, by reacting acrolein and methylmercaptan to obtain 3-methylthiopropionaldehyde, which is successively reacted with hydrogen cyanide.

Hydrolysis reaction of 2-hydroxy-4-methylthiobutyronitrile comprises a hydration reaction of 2-hydroxy-4-methylthiobutyronitrile to 2-hydroxy-4-methylthiobutylamide and a hydrolysis reaction of 2-hydroxy-4-methylthiobutylamide to 2-hydroxy-4-methylthiobutyric acid. Both reactions may be carried out in combination through a single operation, so-called one-step operation, however since the reactions differ in the optimum conditions, it is preferable to carry out the reaction separately in two-stages; that is, a first step reaction for carrying out mainly hydration of 2-hydroxy-4-methylthiobutyronitrile to 2-hydroxy-4-methylthiobutylamide and a second step reaction for carrying out mainly hydrolysis of 2-hydroxy-4-methylthiobutylamide to 2-hydroxy-4-methylthiobutyric acid.

The first step reaction is generally carried out at a temperature of from 40 to 70° C. The use amount of sulfuric acid is generally from 0.5 to 1 mole to 1 mole of 2-hydroxy-4-methylthiobutyronitrile and the use amount of water is generally from 20 to 70 parts by weight to 100 parts by weight of 2-hydroxy-4-methylthiobutyronitrile. Further, it is preferable to adjust sulfuric acid and water in a manner that the use amount of sulfuric acid is 100 to 250 parts by weight to 100 parts by weight of water.

The second step reaction is generally carried out at a temperature of 90 to 130° C. by additionally mixing water and if necessary sulfuric acid to the reaction mixture obtained in the first step reaction. The addition amount of water is generally adjusted to be 50 to 200 parts by weight in the sum with the use amount of water in the first step reaction and the amount of this step to 100 parts by weight of 2-hydroxy-4-methylthiobutyronitrile of the raw material. It is also preferable to adjust the addition amount of water and sulfuric acid in a manner that the sum of the use amount of sulfuric acid in the first step reaction and the addition amount of sulfuric acid is 40 to 100 parts by weight to 100 parts by weight of the sum of the use amount of water in the first step reaction and the addition amount of water.

The reaction mixture containing 2-hydroxy-4-methylthiobutyric acid obtained by the hydrolysis reaction is separated into an oil layer containing 2-hydroxy-4-methylthiobutyric acid and a water layer [step (2)]. In the case where the reaction mixture is obtained in form of an even solution but not a mixture of two layers of oil and water by hydrolysis reaction, the reaction mixture may be converted into a mixture of two layers of oil and water by, for example concentrating the mixture, adding an organic solvent separable from water, or adding a base and successively oil-water separation may be carried out. On the other hand, if the reaction mixture is obtained as a mixture of two layers of oil and water, it may be subjected to oil-water separation as it is or in the same manner as described, oil-water separation may be carried out, for example, after concentration, addition of an organic solvent separable from water, or addition of a base for improving the oil-water separability. In both cases, particularly if the treatment of mixing the base is carried out, the oil-water separability or the distribution ratio of 2-hydroxy-4-methylthiobutyric acid to the oil layer is increased owing to salting-out effect and therefore, it is preferable.

Examples usable for the above-mentioned base are hydroxides such as sodium hydroxide and potassium hydroxide; carbonates such as sodium carbonate and potassium carbonate; bicarbonates such as sodium bicarbonate and potassium bicarbonate; and amonia. The use amount of the base is generally 0.5 to 1.2 moles to 1 mole of ammonium bisulfate contained in the hydrolysis reaction mixture.

At the time of oil-water separation, a sulfate ester may be sometimes precipitated in the water layer, and in such a case, the oil-water separation may be carried out as the mixture is, or the mixture is heated to dissolve the sulfate and then oil-water separation may be carried out, or the sulfate is removed by filtration or decantation and then the oil-water separation may be carried out. The temperature of the oil-water separation is generally from 30 to 120° C.

The oil layer containing 2-hydroxy-4-methylthiobutyric acid obtained by the oil-water separation is successively concentrated [step (3)]. Accordingly, water contained in the oil layer and, in the case of using the organic solvent, the volatile component such as the organic solvent are removed to increase the concentration of 2-hydroxy-4-methylthiobutyric acid. This concentration is generally carried out at a temperature of from 50 to 120° C. in reduced pressure of from 1 to 20 kPa.

In the above-mentioned concentration of the oil layer, 2-hydroxy-4-methylthiobutyric acid is dehydration-condensed with sulfate contained in a small amount in the oil layer to produce a sulfate ester (1-carboxy-3-methylthiopropyl sulfate) aside and it may cause a problem in the quality of the product. Therefore, to suppress the sulfate ester to be produced aside, heating treatment is carried out after the concentration of the oil layer [step (4)].

The sulfate ester is hydrolyzed with water contained in the concentrated product and converted into 2-hydroxy-4-methylthiobutyric acid and sulfuric acid and it is supposed that decrease of the amount of sulfate ester to be produced aside by such heating treatment is owing to promotion of hydrolysis by the heating treatment.

The heating treatment temperature is generally 70° C. or higher, preferably 75° C. or higher, and generally 110° C. or lower, preferably 90° C. or lower. The heating treatment time is generally from 3 to 48 hours and as the duration of the heating treatment is longer, the byproduct, a sulfate ester, tends to be decreased more and as the temperature for the heating treatment is higher, the duration of the heating treatment tends to be shorter. Further, the heating treatment may be carried out in a normal pressure, a reduced pressure, or an increased pressure.

In this connection, the heating treatment of the step (4) and the concentration of the step (3) are discriminated in terms of the constitution and accordingly, the heating treatment is carried out without distilling the volatile component such as water from the concentrated product. For example, in the case where the heating treatment is carried out in temperature and pressure conditions in which water is to be evaporated from the concentrated product, it is required to carry out the heating treatment in refluxing condition by installing a cooling apparatus to condense the evaporated water and turning the condensed water back to the concentrated liquid.

The concentrated product to be subjected to the above-mentioned heating treatment is preferable to be added water to adjust water content at 5% by weight or higher since the sulfate ester byproduct can be efficiently decreased, however if water is so much, the product to be obtained after the heating treatment may possibly have a low 2-hydroxy-4-methylthiobutyric acid content and therefore, it is preferable to adjust the water content to be 15% by weight or lower. Further, in the case where there is an insoluble matter such as a sulfate salt in the concentrated product, the heating treatment is better to be carried out after the insoluble matter is removed by filtration.

The high quality 2-hydroxy-4-methylthiobutyric acid obtained in such a manner is preferably usable for a feed additive for animals, or the like

EXAMPLES

Hereinafter, the present invention will be illustrated along with Examples, however, it is not intended that the present invention be limited to the illustrated Examples. In explanation of Examples, % expressing the content means % by weight unless otherwise specified.

Example

A 2 liter four-necked flask was loaded simultaneously with 694.35 g (5 moles) of 94.5% 2-hydroxy-4-methylthiobutyronitrile and 544.01 g of an aqueous 63% sulfuric acid solution at 55° C. for 30 minutes and the mixture was mixed and further kept at 50° C. for 1 hour. Further, 3 g of an aqueous 63% sulfuric acid solution and 574.75 g of water were added to the mixture, and after the contents were heated and refluxed (at an inner temperature of 109° C.) for 4 hours, 36.32 g of low boiling point components were removed by distillation to obtain 1779.79 g of a reaction solution containing 2-hydroxy-4-methylthiobutyric acid.

After 24.93 g of an aqueous 48% sodium hydroxide solution was added to 380 g of the reaction solution at 100 to 110° C., the mixture was kept at the same temperature for 1.5 hours and successively, oil-water separation was carried out at the same temperature to obtain 252.44 g of an oil layer and 148.65 g of a water layer. The oil layer was concentrated at 100° C. in reduced pressure of 30 mmHg (3.9 kPa) for 1 hour to obtain 182.4 g of a concentrated liquid containing solid matter (a sulfate salt). The concentrated liquid was filtered for separating the solid matter and 13.7 g of water was added to 122.8 g of the obtained filtrate. The obtained liquid was analyzed by high performance liquid chromatography to find that the content of 2-hydroxy-4-methylthiobutyric acid was 68.13%: that the content of compounds (two kinds of diastereomers) obtained by dehydration-condensation of two molecules of 2-hydroxy-4-methylthiobutyric acid was 20.07% (10.79% and 9.28%): and that the ratio of a sulfate ester byproduct (1-carboxy-3-methylthiopropyl sulfate) to 2-hydroxy-4-methylthiobutyric acid was $3,626 \times 10^{-3}$ by the peak area ratio in the chromatogram. Further, the obtained liquid was analyzed by Karl Fischer technique to find that the content of water was 10.84%. Thereafter, after the liquid was heated at 80° C. for 24 hours, the above-mentioned peak area ratio was decreased to $1.927 \times 10^{-3}, 1.153 \times 10^{-3}, 0.616 \times 10^{-3}$, and to $0.149 \times 10^{-3}$, after 3 hours, 6 hours, 10 hours, and 24 hours, respectively.

According to the present invention, a process for producing high quality 2-hydroxy-4-methylthiobutyric acid with suppressed sulfate ester production aside is provided.

What is claimed is:

1. A process for producing 2-hydroxy-4-methylthiobutyric acid comprising the following steps (1) to (4):
   (1): hydrolyzing 2-hydroxy-4-methylthiobutyronitrile in the presence of sulfuric acid,
   (2): separating the reaction mixture obtained in the step (1) into an oil layer containing 2-hydroxy-4-methylthiobutyric acid and a water layer,
   (3): concentrating the oil layer obtained in the step (2), and
   (4): heating the concentrated product obtained in the step (3) without distilling a volatile component from the concentrated product.

2. The process according to claim 1, wherein after the concentrated product obtained in the step (3) is mixed with water to adjust the water content to be 5 to 15% by weight, the concentrated product is heated in the step (4).

3. The process according to claim 1 or 2, wherein the heating temperature in the step (4) is 70° C. or higher.

* * * * *